United States Patent [19]

Eiseman

[11] 4,203,757
[45] May 20, 1980

[54] HALOPHENOXYALKOXY PHOSPHOROUS-CONTAINING SULFIDES

[75] Inventor: Fred S. Eiseman, Basking Ridge, N.J.

[73] Assignee: GAF Corporation, New York, N.Y.

[21] Appl. No.: 938,373

[22] Filed: Aug. 31, 1978

[51] Int. Cl.² ............... A01N 9/36; C07F 9/141; C07F 9/165
[52] U.S. Cl. .................. 71/87; 260/929; 260/978; 260/985
[58] Field of Search .......... 260/929, 978, 985; 71/87

[56] References Cited

U.S. PATENT DOCUMENTS

| 2,571,989 | 10/1950 | Schrader | 260/929 X |
| 3,641,219 | 2/1972 | Stockburger | 260/929 OR |

Primary Examiner—Anton H. Sutto
Attorney, Agent, or Firm—Walter C. Kehm; Marilyn J. Maue

[57] ABSTRACT

The halophenoxy-alkoxy phosphorous-containing sulfides of the present invention are represented by the general formula:

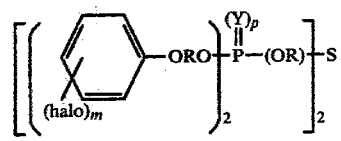

wherein
each R is alkylene having from 1 to 3 carbon atoms;
Y is O or S;
m is an integer from 1 to 3;
p is O or 1
and wherein
P is trivalent when p is O and pentavalent when p is 1.

These compounds are particularly useful as herbicides, algicides and lubricants or lubricant additives.

18 Claims, No Drawings

HALOPHENOXYALKOXY PHOSPHOROUS-CONTAINING SULFIDES

The present invention relates to novel compounds having herbicidal activity on weeds, e.g. chickweed, lambsquarter, quackgrass, bindweed, etc., and can be applied to growing or seedling plants or can be applied to the plant situs in a pre-emergent treatment. The present compounds are also useful lubricants or lubricant additives for gears and other metal working parts.

The halophenoxy-alkoxy phosphorous-containing compounds of this invention are described by the formula:

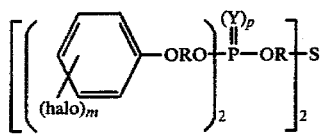

wherein
each R is alkylene having from 1 to 3 carbon atoms;
Y is O or S;
m is an integer from 1 to 3;
p is 0 or 1
and wherein
P is trivalent when p is 0 and is pentavalent when p is 1.

These compounds are referred to herein as bis(halophenoxyalkoxy)phosphoalkyleneoxy sulfides.

Specific examples of the present compounds include chlorinated, brominated, fluorinated and iodinated phenoxyethoxy phosphonate- and thiophosphonate-ethylester sulfides; said halogenated phenoxymethoxy phosphonate- and thiophosphonate-ethylester sulfides; said halogenated phenoxymethoxy phosphonate- and thiophosphonate-methyl ester sulfides; said halogenated phenoxypropoxy phosphonate- and thiophosphonate-ethylester sulfides; said halogenated phenoxypropoxy phosphonate- and thiophosphonate-propylester sulfides; said halogenated phenoxymethoxy phosphite methylester sulfides; said halogenated phenoxyethoxy phosphite ethylester sulfides; said halogenated phenoxypropoxy phosphite propyl ester sulfides; said halogenated phenoxyethoxy phosphite methylester sulfides; said halogenated phenoxymethoxy phosphite ethyl ester sulfides, etc. Of these, the sulfides wherein all R groups represent the same alkylene radical are preferred; and, of these, the sulfides wherein m is 2 and halo is chloro or bromo are most preferred.

The compounds of this invention may be conveniently prepared by reacting an excess of a bis-(halogenated phenoxyalkoxy)phosphino-hydroxide with a dialkanol sulfide (or thiodialkanol) to provide the corresponding tertiary phosphine compound, i.e. [bis(-halophenoxyalkoxy)alkyleneoxy phosphino]sulfide. The later compound may then be reacted with sulfur or oxygen to provide the corresponding thiophosphonate or the phosphonate derivative.

The halogenated phenoxyalkoxy phosphino hydroxides are prepared by reacting a correspondingly halogenated phenoxy alkanol with phosphorous acid or a mixture of phosphorous and hypophosphorous acids, preferably employed in stoichiometric amount, at a temperature of between about 50° C. and about 150° C. under from about 10 psig. to about 50 psig.

The resulting bis(halophenoxyalkoxy)phosphinohydroxide is then mixed with a thiodialkanol in a mole ratio of between about 1.5:1 and about 10:1 or excess of the phosphino compound and reacted at a temperature of between about 30° C. and about 180° C. under a pressure of from 10 psig to about 100 psig; preferably at a temperature of between about 80° C. and about 160° C. under atmospheric pressure, for a period of from about 20 minutes to about 5 hours, to produce said [bis-(halophenoxyalkoxy)phosphino alkyleneoxy]sulfide wherein the phosphorous is trivalent.

To produce the product wherein the phosphorous is pentavalent, the above trivalent product is contacted with finely divided or powdered sulfur or oxygen gas, oxygen enriched with ozone, hydrogen peroxide or a compound which generates oxygen in situ to provide respectively the thiophosphonate or phosphonate derivatives of the present invention. The conversion to phosphonates or thiophosphonates is carried out under the same ranges of operating conditions as those employed in the reaction involving thiodialkanol.

The generic formulae for the preparation of the present compounds are as follows:

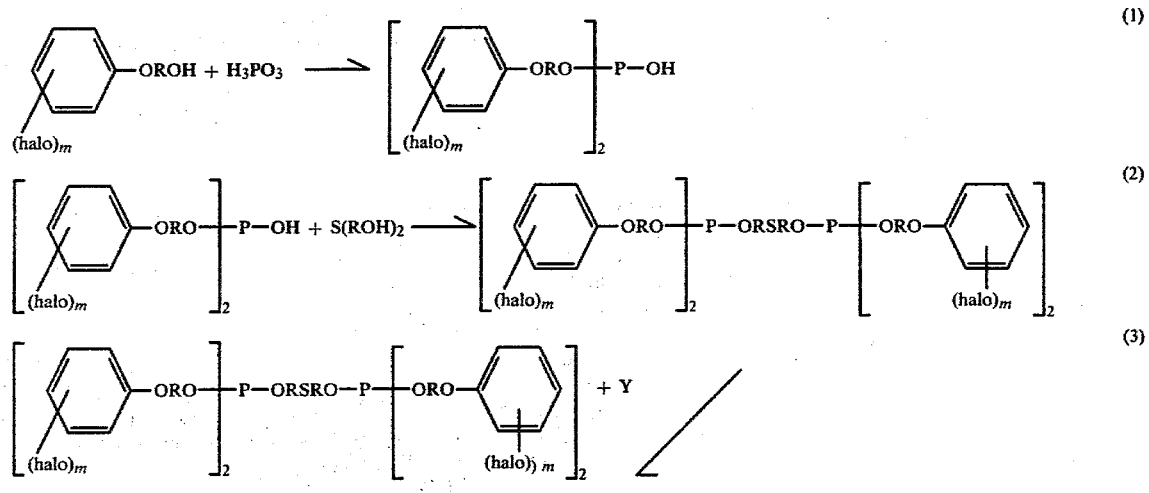

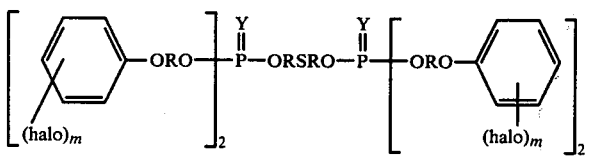

wherein
- Y is oxygen or sulfur;
- m is an integer from 1 to 3 and
- each R is alkylene having from 1 to 3 carbon atoms.

For best results, it is recommended that in reaction (1) the mixture be constantly agitated and that the phosphorous acid reactant be added to the halophenoxy alkanol prior to reaction or introduced intermittantly during reaction. Alternatively, a mixture of these reactants can be introduced simultaneously into the reactor and the reaction carried out, with agitation, in a closed or open system. The reactions may be effected in the absence or in the presence of a solvent such as benzene, toluene, xylene, cyclohexane, or any other inert organic liquid preferably of paraffin series.

By selection of the particular halophenoxyalkanol employed in the preparation, the value of m and R can be varied. Representative of the phenoxyalkanols which may be employed are:

- 2,3, or 4-chlorophenoxy methanol
- 2,3, or 4-chlorophenoxy ethanol
- 2,3, or 4-chlorophenoxy propanol
- 2,4-, 3,4- or 2,3-dichlorophenoxy methanol
- 2,4-, 3,4- or 2,3-dichlorophenoxy ethanol
- 2,4-, 3,4- or 2,3-dichlorophenoxy propanol
- 2,3,4-trichlorophenoxy ethanol
- 2,3,4-trichlorophenoxy propanol
- and the corresponding fluoro-, bromo- or iodo-derivatives of the above compounds and mixtures thereof.

Examples of dialkanol sulfides which may be reacted with the halophenoxyalkoxy phosphino hydroxides include dimethanol sulfide, diethanolsulfide, dipropanol sulfide, methyl ethyl sulfide, ethyl propylsulfide and mixtures thereof.

Generally the phosphino sulfides, phosphonate sulfides and thiophosphonate sulfides are light colored solids at ambient temperature soluble in most polar solvents, particularly alchohols and ethers; and miscible with water.

Reference is now had to the following examples which illustrate preferred embodiments, but which are not to be construed as limiting to the scope of this invention as defined in the foregoing disclosure and in the accompanying claims.

EXAMPLE I

To a 500 ml flask, 310 grams of 2,4-dichlorophenoxy ethanol and 2 grams of hypophosphorous acid are charged and the contents agitated at room temperature. The mixture is heated to 40°–45° C. and 255 grams of phosphorous acid is gradually added over a period of one hour, after which the flask is slowly heated up to 90°–95° C. and held at that temperature for an additional 4 hours. The orange colored ester mixture of the following formulae, solidified when cooled to room temperature. The diacid was removed by extraction with benzene, and the monoacid recovered in about 40% yield.

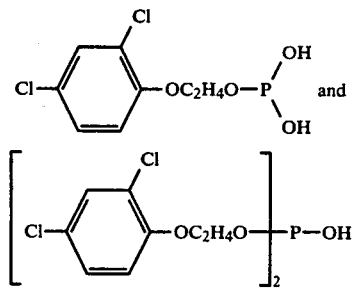

It is to be understood that any of the above mono-, di-, or tri-halogenated (i.e. fluorinated, chlorinated, brominated or iodinated) phenoxy-alkanol compounds such as the methanol, ethanol or propanol, can be substituted in the above example to provide the corresponding product.

EXAMPLE II

A. Into a glass autoclave is added 226 grams of thiodiethanol, 600 grams of the above P,P-bis(2,4-dichlorophenoxyethoxy)phosphite acid ester and the components are constantly agitated at a gradually increasing temperature of 105°–135° C. for 2 hours. The product:

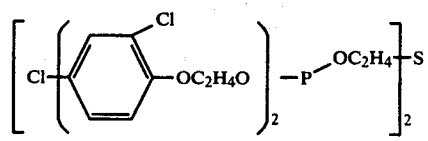

formed in about 60% yield, solidifies upon cooling and is recovered as a light solid.

B. About 160 grams of the above product from A is then treated with 13 grams of powdered sulfur is aqueous solution at a temperature of between 130° and 145° C. for about one hour, after which the product is cooled and solidified to a light solid having the following formula:

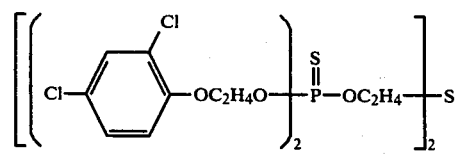

C. Oxygen gas is bubbled through 100 grams of the product of A. for a period of 2 hours at a temperature of 135° C. A light-colored solid product forms upon cooling to room temperature.

The product formed is

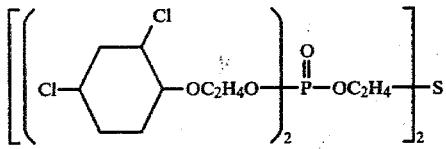

It is to be understood that any of the halophenoxy alkanol products referred to in Example I can be substituted in IIA for the P,P-bis(2,4-dichlorophenoxyethoxy)phosphite acid ester and that any of the thiodialkanol reactants specified herein such as thiodimethanol, thiodipropanol, thiomethylethyl, can be substituted for thiodiethanol in IIA to provide the corresponding [P,P-bis(halophenoxyalkoxy)alkyleneoxy phosphino]sulfide product and that any of such products can be reacted with sulfur or oxygen according to the procedure set forth in IIB and IIC to provide the corresponding thiophosphonate and phosphonate-sulfides of this invention.

EXAMPLE III

A. Example IIA is repeated except that thioethanolpropanol is substituted for thiodiethanol therein. The product obtained is

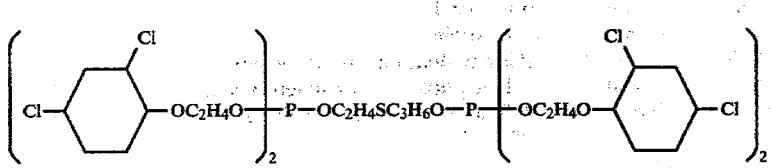

B. The corresponding phosphonate and thio phosphonate sulfides are prepared according to the procedure set forth in IIB and IIC, except that product IIIA above is substituted for product IIA.

When the compounds of the present invention are employed as herbicides, it is recommended from the standpoint of economy that they be mixed with a liquid or particulate solid carrier extender or adjuvant which is inert with respect to the present herbicide. Examples of suitable carriers include water, hydrocarbon alkanes of from 4 to 10 carbon atoms, benzene, xylene, toulene, a mineral oil fraction, a vegetable oil, etc. The adjuvant as used herein, includes one or more materials in liquid or solid form. Thus, suitable adjuvants include diluents, surfactants, foaming agents, conditioning agents, solvents and combinations thereof. The compositions can be in numerous forms, such as, dusts, powders, water soluble powders, wettable powders, solutions, foams, dispersions or emulsions. Generally, it is preferred to use one or more surfactants in the plant growth-regulating compositions which aid in wetting the treated plant surface and for providing stable dispersions of the active ingredient in various inert carriers or diluents in the composition or added to the composition prior to application to the plants. Suitable surfactants which can be employed in the compositions of this invention are well known surface active agents, such as, wetting agents, emulsifiers, dispersing agents and can be nonionic, anionic or cationic. Preferred surfactants are the nonionic or the anionic type which are widely used in compositions employed in agronomic treatments. Representative nonionic surfactants are polyoxyethylene esters of fatty acids, octylphenyl polyethylene glycol ethers, polyoxyethylene derivatives of long-chain alcohols and the like. Representative anionic surfactants are alkali and alkaline earth salts of alkyarylsulfonic acids such as sodium lauryl sulfonate, dialkyl sodium sulfosuccinate esters and the like.

Usually the plant growth-regulating compositions of this invention take the form of a concentrate which can be readily extended with an inert carrier prior to application of the plants. Said concentrates in liquid form consist of a solvent, surfactant and about 25 to 75% by weight of the active ingredient. These liquid concentrates can be diluted with water to provide a composition, suitable for application to plants, which contains from about 0.1 to about 15% by weight of the active ingredient. Concentrates in solid form are, for example, water soluble powders consisting of finely divided solids such as calcium silicate surfactant and from about 5 to 80% or more by weight of the active ingredient which are diluted with water prior to applying to the plants.

A representative plant growth regulating composition in the form of a concentrate contains approximately 8 parts of nonylpheonl-ethylene oxide condensate (STEROX NJ, surfactant), 4 parts of calcium silicate (Microcel E, absorbent) blended sufficiently to absorb the liquid surfactant. About 8 parts of monoammonium phosphate is added to the blend which is then added to 80 parts of the present herbicide in a suitable powder blender to form a uniform mixture of the active ingredient in the form of a free flowing powder which is substantially soluble in water.

It is to be understood, however, that the present herbicides can also be employed without the addition of any surfactant or additive other than the carrier or extender. In these cases, the concentration of the herbicide in the carrier is between about 200 ppm and about 15,000 ppm; preferably between about 1,000 ppm and about 10,000 ppm.

The herbicide is applied to a plant or plant situs at 0.2 to 20 grams per hectare. The present herbicides, when applied to the pre-emergent plant situs prevents emersion of chickweed and controls noxious weeds such as for example chickweed, lambsquarter when applied to growing plants.

As an algicide, the present compounds may be used in swimming pools, wherein effective amounts of the compound are between 5 and 500 ppm.

EXAMPLE IV

When an aqueous solution containing about 5,000 ppm of the herbicidal agents of this invention is applied at about 8 lbs/acre to a field wherein mustard and pigweed are growing with wheat, rye, oats or barley, 75 to 85% of the mustard and pigweed undergo severe injury while the graminae crop is practically uneffected.

More complete control is realized when the field is treated before sprouting of the weed. Particularly active agents are:

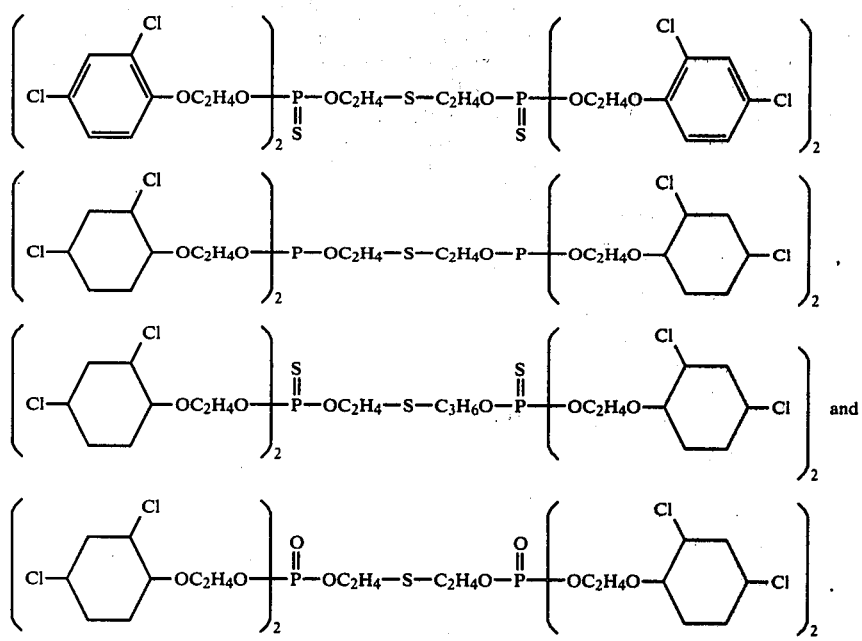

The products of the present invention, when employed in aqueous dispersions, or alcoholic or oil solutions, for example of between about 0.01% and about 1% concentration of the present sulfide, are beneficial as antiwear agents and lubricants for heavy machinery. Aqueous dispersions containing up to about 10% of the above products are also useful in several agronomic applications, e.g. control of mildews when applied to the soil at a rate of between about 1 and about 20 pounds per acre, e.g. as preventative for powdery mildew. Still further they are generally useful as oil additives in cutting oils, mineral lubricating oils of petroleum origin and synthetic lubricants. The present products also find application as greases, rust preventatives, etc.

Many modifications and variations of the present invention will become apparent from the above disclosure, however, it is to be understood that these are also included within the scope of the present invention.

I claim:

1. A bis-(halophenoxyalkoxy)phosphino alkoxy sulfide having the formula:

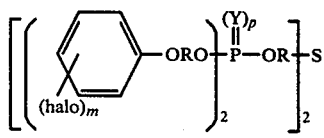

wherein
each R is alkylene having from 1 to 3 carbon atoms;
Y is oxygen of sulfur
m is an integer having a value of from 1 to 3;
p is 0 or 1
and wherein
P is trivalent phosphorous when p is 0 and is pentavalent phosphorous when p is 1.

2. The compound of claim 1 having the formula:

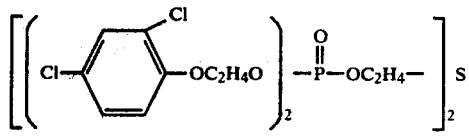

3. The compound of claim 1 having the formula:

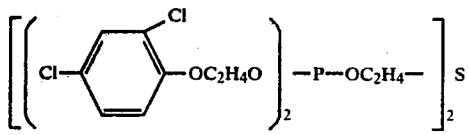

4. The compound of claim 1 having the formula:

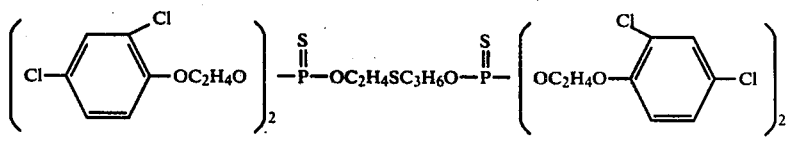

5. The compound of claim 1 having the formula:

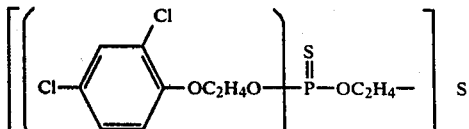

6. The process for inhibiting the growth of weeds which comprises contacting the plant or plant situs with a herbicidally effective amount of the compound of claim 1.

7. The process of claim 6 wherein the compound of claim 2 is employed.

8. The process of claim 6 wherein the compound of claim 3 is employed.

9. The process of claim 6 wherein the compound of claim 4 is employed.

10. The process of claim 6 wherein the compound of claim 5 is employed.

11. A process for preparing the bis(halophenoxyalkoxy)phosphino alkoxy sulfide of claim 1 which comprises: contacting an excess of bis(halophenoxylakoxy)phosphino hydroxide having the formula

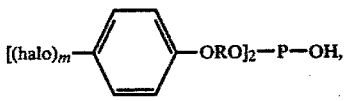

wherein halo, m and R are defined in claim 1, with a thiodialkanol at elevated temperature.

12. The process of claim 11 wherein the reaction is carried out at a temperature of between about 30° C. and about 180° C., under from about 10 psig to about 100 psig.

13. The process of claim 11 wherein the reaction is carried out at a temperature of between about 80° C. and about 160° C. under atmospheric pressure, with continuous agitation.

14. The process of claim 11 wherein the mole ratio of bis(halophenoxylalkoxy)phosphino hydroxide to said thiodialkanol is between about 1.5:1 and about 10:1.

15. The process of claim 11 wherein the product of the reaction is contacted with sulfur powder or oxygen at elevated temperature to produce the corresponding thiophosphonate or phosphonate sulfides of claim 1.

16. The process of claim 15 wherein the reaction with powdered sulfur or oxygen is effected at a temperature of between about 30° C. and about 180° C., under from about 10 psig. to about 100 psig.

17. A herbicidal composition comprising a herbicidally effective amount of at least one compound of claim 1 and an inert liquid carrier therefor.

18. A herbicidal composition comprising a herbicidally effective amount of at least one compound of claim 1 and an inert particulate solid carrier therefor.

* * * * *